(12) United States Patent
Heath et al.

(10) Patent No.: US 8,154,390 B2
(45) Date of Patent: Apr. 10, 2012

(54) SYSTEM AND METHOD FOR AUTOMATING AND VERIFYING MEDICATION COMPLIANCE

(75) Inventors: Chester Heath, Boca Raton, FL (US); Pedro Martinez, Boca Raton, FL (US)

(73) Assignee: The Quantum Group, Wellington, FL (US)

( * ) Notice: Subject to any disclaimer, the term of this patent is extended or adjusted under 35 U.S.C. 154(b) by 356 days.

(21) Appl. No.: 12/470,550

(22) Filed: May 22, 2009

(65) Prior Publication Data

US 2010/0298975 A1 Nov. 25, 2010

(51) Int. Cl.
*G08B 1/00* (2006.01)

(52) U.S. Cl. .................. 340/309.16; 340/539.12

(58) Field of Classification Search ........... 340/309.16, 340/539.12, 573.1, 309.7; 368/10; 705/2
See application file for complete search history.

(56) References Cited

U.S. PATENT DOCUMENTS

| | | | | |
|---|---|---|---|---|
| 4,617,557 A * | 10/1986 | Gordon | ...................... | 340/309.7 |
| 5,412,372 A * | 5/1995 | Parkhurst et al. | .......... | 340/568.1 |
| 6,380,858 B1 * | 4/2002 | Yarin et al. | ................. | 340/573.1 |
| 6,670,885 B2 * | 12/2003 | Kosaka | ..................... | 340/309.16 |
| 6,973,371 B1 * | 12/2005 | Benouali | ......................... | 368/10 |
| 7,230,521 B2 * | 6/2007 | Terenna | ................... | 340/309.16 |
| 7,366,675 B1 * | 4/2008 | Walker et al. | ..................... | 705/2 |
| 7,755,478 B2 * | 7/2010 | Niemiec et al. | .......... | 340/539.12 |
| 7,928,835 B1 * | 4/2011 | Jovanov et al. | .......... | 340/309.16 |
| 7,956,727 B2 * | 6/2011 | Loncar | ..................... | 340/309.16 |

* cited by examiner

*Primary Examiner* — John A Tweel, Jr.
(74) *Attorney, Agent, or Firm* — Novak Druce + Quigg LLP

(57) ABSTRACT

A computer-based system for monitoring medication compliance. The system can include one or more processors configured to process and manage data. Additionally, the system can also include one or more medication packagings comprising a machine-readable medium. Notably, the machine-readable medium can comprise medication information among other types of information. The one or more processors can be configured to receive the medication information of the machine-readable medium. The machine-readable medium and corresponding medication information can be adjustable based on a dispensing of a medication from the one or more medication packagings.

27 Claims, 9 Drawing Sheets

SYSTEM AND METHOD FOR AUTOMATING AND VERIFYING MEDICATION COMPLIANCE

FIELD OF THE INVENTION

The present invention is related to the fields of medication dosage control and medication compliance, and more particularly, to computer-based systems and methods for automating and verifying patient compliance with a particular medication regimen.

BACKGROUND OF THE INVENTION

Advances in patient care have helped to dramatically increase patients' lifespans and quality of life through the development of more effective treatments, medications, and medical technologies. Despite these advances, a leading cause of medical patient fatalities is accidental patient non-compliance with pharmaceutical dosage programs. For example, many patients often forget to take their medications, take too many doses of their medications, take the wrong medications, or take their medications in an incorrect manner. Additionally, some patients even forget to fill their prescriptions in the first place. As a result, taking medications in a non-compliant fashion often leads to a prolonging of disease-related symptoms, an increase in serious complications, unnecessary additional medical visits, higher medical costs, and possibly even death.

People often use the assistance of calendars, physicians, other people, their own memory, and other methods to help remind them to take a particular medication or to help verify that they took the medication according to the proper regimen. However, such methods often fail to adequately remind the patient to take their medications on a regular basis or in an effective manner. Such methods further fail to verify that the patient actually took the medication appropriately.

SUMMARY OF THE INVENTION

The present invention is directed to systems and methods for providing an automated mechanism for contacting and reminding patients to take their various medications and/or conform to a particular medical regimen. Also, the present invention is directed to systems and methods for verifying that a particular patient has taken his or her medication at the proper time, in the proper sequence, and/or in the proper dosage amount.

One embodiment of the invention is a computer-based system for monitoring medication compliance. The system can include one or more processors configured to process and manage data. Additionally, the system can also include one or more medication packagings comprising a machine-readable medium. The machine-readable medium can comprise medication information among other types of information. The one or more processors can be configured to receive the medication information of the machine-readable medium. Notably, the machine-readable medium and corresponding medication information can be adjustable based on a dispensing of a medication from the one or more medication packagings.

Another embodiment of the invention is a computer-based method for monitoring medication compliance. The method can include accessing a communications device associated with a patient by utilizing a processor. The method can also include instructing the patient to take one or more medications associated with a medication packaging by utilizing one or more of the processor and the communications device. Furthermore, the method can include determining a condition of the medication packaging.

The invention can also include a medication packaging, which can be utilized in the system described above or otherwise. The medication packaging can include one or more object holders. Also, the medication packaging can include a machine-readable medium, which can be operably coupled to the one or more object holders. The machine-readable medium can be adjustable upon dispensing an object from the one or more object holders.

Yet another embodiment of the invention is a computer-readable medium which contains computer-readable code that when loaded on a computer causes the computer to: access a communications device associated with a patient by utilizing a processor; instruct the patient to take a medication associated with a medication packaging by utilizing one or more of the processor and the communications device; determine if the medication was dispensed from the medication packaging.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
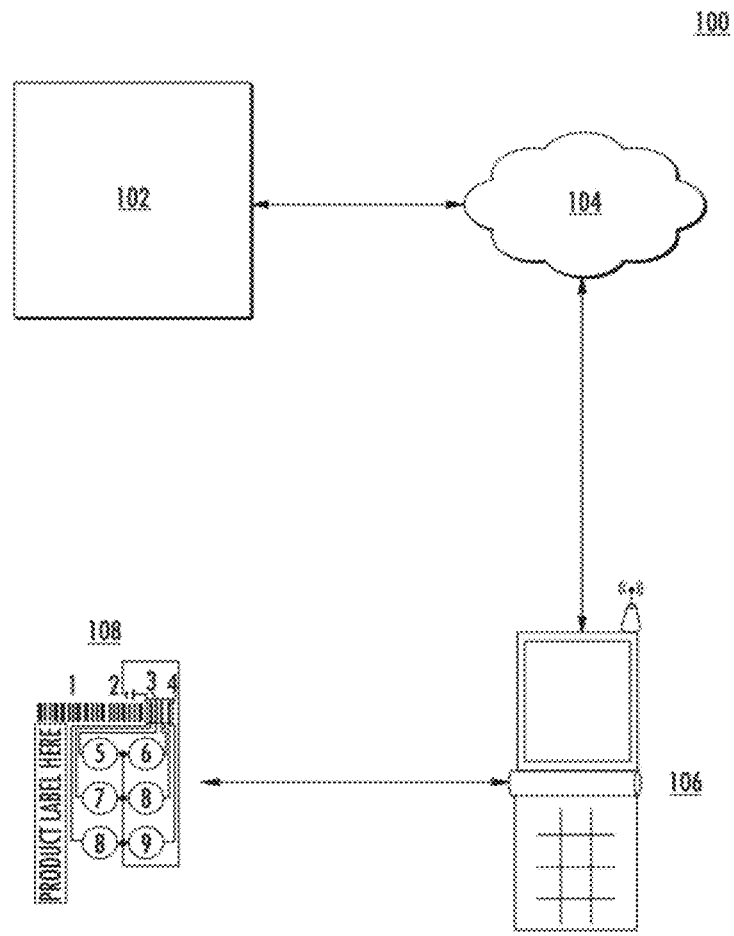
FIG. 1 is a schematic view of a system for monitoring medication compliance, according to one embodiment of the invention.

Referring initially to FIG. 1, a system 100 for monitoring medication compliance, according to one embodiment of the invention, is schematically illustrated. The system can include a processor 102 configured to process and manage data. The system 100 can also include a communications network 104 and a communications device 106. The communications device 106 can be a personal digital assistant (PDA), cellular telephone, land-line phone, mobile device, computer, or other device. Notably, the communications device 106 can be communicatively linked to the processor 102 via the communications network 104 or otherwise. Additionally, the system 100 can include a medication packaging 108. The medication packaging 108 can include, but is not limited to including, a machine-readable medium, wherein the machine-readable medium can comprise medication information or other types of information.

The machine-readable medium can be a barcode, optical disk, magnetic disk, readable card, readable tape, magnetic strip, radio frequency tag, or other machine-readable medium. Also, the medication information included in the machine-readable medium can describe, but is not limited to describing, the medication included in the medication packaging 108 in a manner that is consistent with the labeling on the package itself. Even though one processor 102, one communications network 104, one communications device 106, and one medication packaging 108 are shown, it will be apparent to one of ordinary skill based on the description that a greater number of processors, communications networks, communications devices, and medication packagings can be used according to the invention.

Notably, the processor 102 can be implemented in hardwired, dedicated circuitry for performing the operative functions described herein. In another embodiment, the processor 102 can be implemented in computer-readable code configured to execute on a particular computing machine. In yet another embodiment, however, the processor 102 can be implemented in a combination of hardwired circuitry and computer-readable code.

Operatively, the processor 102 can be configured to receive the medication information of the machine-readable medium and the processor 102 can store and process the medication information. Notably, the machine-readable medium and corresponding medication information can be adjustable based on a dispensing of a medication from the medication packaging 108. In a particular embodiment, the processor 102 can be configured to communicatively link to the communications device 106. The patient can be instructed by the communications device 106 and/or the processor 102 to take one or more medications associated with the medication packaging 108. For example, the processor 102 can place an automated call to the patient's cellular phone, wherein the call can include a reminder telling the patient to take a certain quantity of medication from the medication packaging 108.

The processor 102 and/or the communications device 106 can then be configured to determine a condition of the medication packaging 108. The condition of the medication packaging 108 can indicate, but is not limited to indicating, that a medication from the medication packaging has been dispensed, that the medication and/or medication packaging 108 has expired, that the patient complied with the instructions, or that the medication packaging 108 has or has not been tampered with. In order to determine the condition of the packaging, the processor 102 and/or the communications device 106 can include a device/reader capable of retrieving the medication information from the adjustable machine-readable medium. For example, a barcode scanner can be utilized to read an adjustable barcode contained on the medication packaging 108.

Instead of or in addition to utilizing a reader to retrieve the information from the machine-readable medium, the communications device 106 can capture and store an image (such as through photographing) of the machine-readable medium. The communications device 106 can then automatically read the medication information from the image of the machine-readable medium. The machine-readable medium can be read and the medication information can be stored and managed by the processor 102 and/or the communications device. Notably, the medication information can be forwarded to the processor 102 by the communications device 106.

According to one embodiment, the processor 102 and/or the communications device 106 can be configured to determine if the medication packaging 108 is in an unused state. An unused state can occur when the machine-readable medium has not been adjusted. For example, if the patient did not take the medication as instructed and did not tamper with the medication packaging 108, the machine-readable medium would not be adjusted because no medication was dispensed. When the machine-readable medium is read, the unadjusted machine-readable medium would indicate that the medication packaging 108 was unused.

In another embodiment, the processor 102 and/or the communications device 106 can be configured to determine if the medication has been dispensed from the medication packaging 108. The medication can be indicated as being dispensed if a portion of the machine-readable medium has been adjusted. The portion of the barcode to be adjusted can correspond to the medication. For example, if the patient dispensed the medication from the medication packaging 108, then a portion of a barcode would be adjusted to reflect the fact that the medication was dispensed. After reading the adjusted barcode, the communications device 106 can determine that the medication was indeed dispensed. In yet another embodiment, the processor 102 and/or communications device 106 can be configured to acknowledge/verify that the medication was dispensed from the medication packaging 108. As an illustration, the communications device 106 can display "Medication X has been dispensed" to the patient after reading an adjusted machine-readable medium. In still another embodiment, the processor 102 and/or communications device can provide a reward to the patient for having successfully taken/dispensed their medication. For example, the communications device 106 can retrieve and display a digital gift certificate, coupon, or other reward to the patient after verifying that the medication dispensed.

Figure 2:
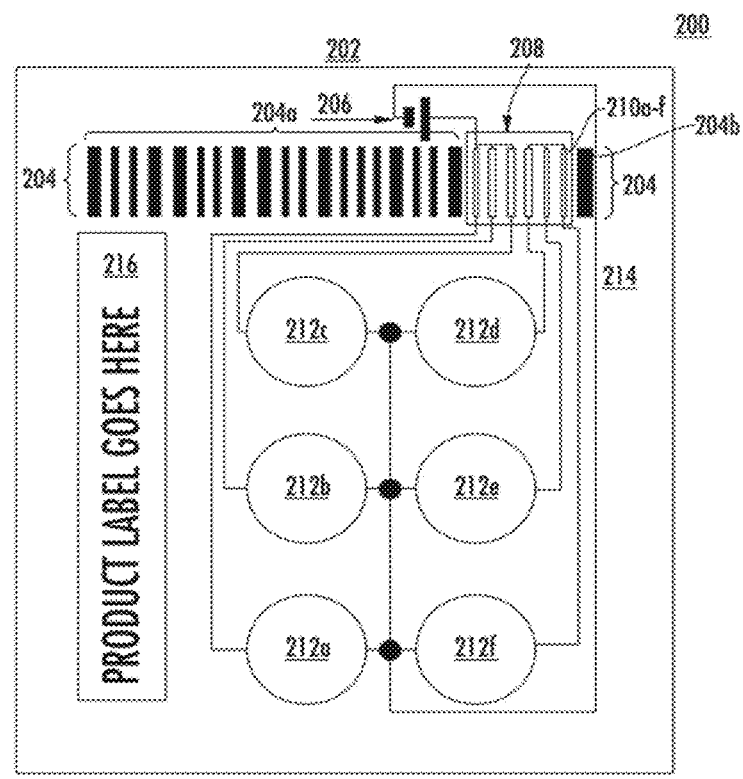
FIG. 2 is a schematic view illustrating a medication packaging including an adjustable barcode according to the invention.

Referring now also to FIG. 2, a schematic view illustrating a medication packaging 200 including an adjustable barcode according to the invention is shown. Notably, the medication packaging 200 can be utilized in the system 100. The medication packaging can include a card 202 having a top and bottom surface. Notably, the card 202 can be made of cardboard or other materials. The medication packaging 200 can also include a machine-readable medium, such as barcode 204, an optical disk, a magnetic disk, a readable card, a readable tape, a magnetic strip, a radio frequency tag, and/or other machine-readable mediums. The barcode 204 can include a barcode preamble 204a, which can describe, but is not limited to describing, the medication contained in the medication packaging 200 in a manner that is consistent with the package labeling 216. Additionally, the barcode can include a printed stop bit 204b or other character, which can indicate the end of the barcode sequence.

In an embodiment, the medication packaging 200 can also include a power source 206, a swatch of thermal sensitive paper 208, an array of resistive strips 210a-f (the farthest left resistive strip being 210a), and a series of object/medication holders 212a-f. In this case, the power source 206 can be a battery. The thermal sensitive paper 208 can reside over the array of resistive strips 210a-f, which can reside adjacent to a portion of the barcode 204. In FIG. 2 the thermal sensitive paper 208 is between the preamble 204a and the stop bit 204b. The series of object holders 212a-f can be a blister-pack technology for containing a number of medications, which can be in pill and/or liquid form. Notably, the power source 206 can be operably coupled to the array of resistive strips 210a-f, the barcode 204, and the object holders 212a-f via wires 214. The barcode 204 can be adjustable upon dispensing an object from the an object holder of the object holders 212a-f.

Figure 3A:
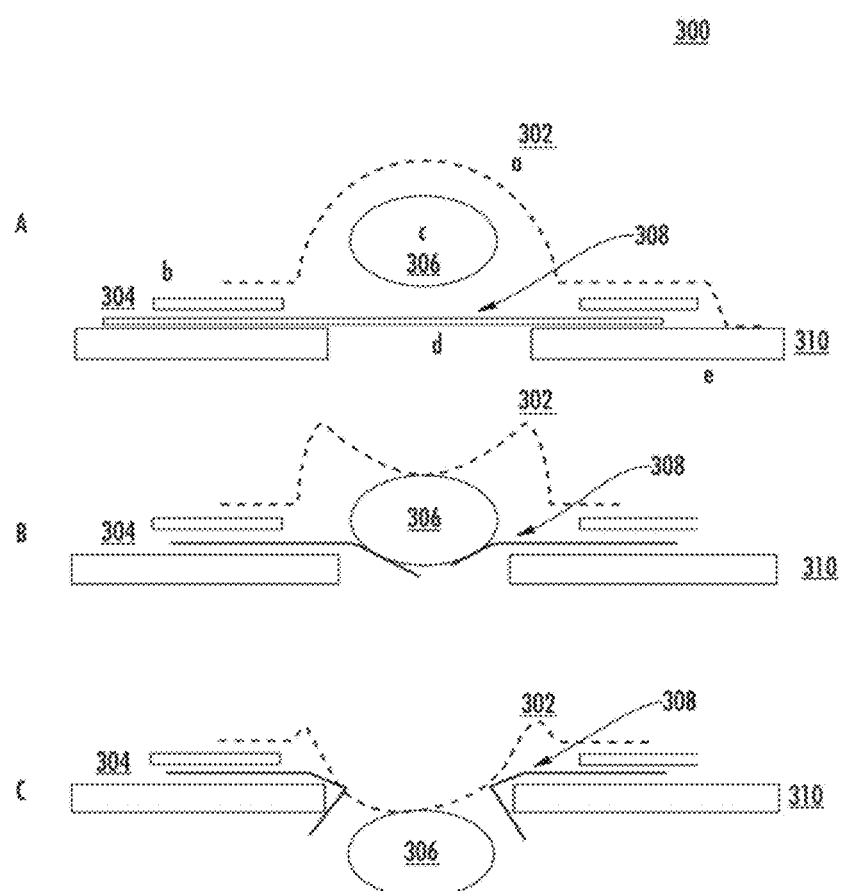
FIG. 3A is an illustration depicting a side view of a dispensing sensor, which can be included in a medication packaging.
Figure 3B:
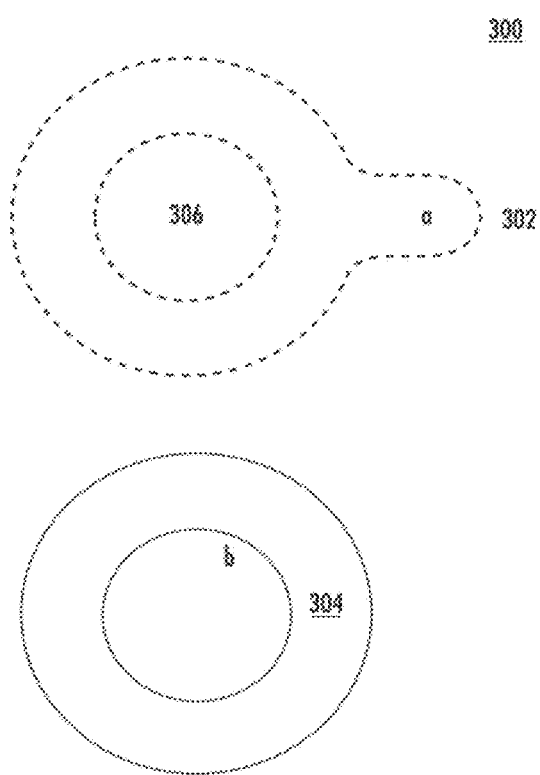
FIG. 3B is an illustration depicting a top view of the dispensing sensor.

Referring now also to FIG. 3A, a side view of an object holder/dispensing sensor 300 undergoing various states (A), (B), and (C) is illustratively shown. In an embodiment, each object holder 212a-f can serve as a specialized contact switch and can comprise a conductive cover 302, an insulator 304, and a conductive foil 308. The object holders 212a-f can include a medication 306 and can reside on a card 310. The conductive foil 308 can be embossed with preferential patterns for tearing. Referring now also to FIG. 3B, a top view of the object holder/dispensing sensor 300 is shown, which shows the conductive cover 302 and the medication 306 separately from the insulator 304. Referring back to FIG. 3A, state (A) illustrates the object holder 300 in a normal state with the medication 306 contained within the object holder 300.

According to another embodiment, the conductive cover 308 can be depressed, which can cause the conductive foil 308 to tear and release the object/medication 306 from the object holder 300 via the hole in the card 310. State (B) illustrates the conductive cover 302 being depressed and the tearing of the conductive foil 308. In another embodiment, the conductive cover 302 can contact the conductive foil 308 (state (C)), thereby closing a circuit with the power source 206 to at least one resistive strip of the array of resistive strips 210a-f. This can cause the resistive strips 210a-f to rapidly heat and self destruct, wherein the heating and destruction process can cause the thermal sensitive paper 208 to create a readable image on the thermal sensitive paper 208. The effect of creating the readable image, for example, is to create a bar or to extend a bar, such that at least one "bit" of the full barcode 204 is altered. This effectively adjusts the barcode 204, which can now indicate which medication 306 was dispensed. As an illustration, if the conductive cover 302 for object holder 212a contacts the conductive foil 308, the resulting closed circuit can cause resistive strip 210a to self-destruct, thereby creating a readable bar corresponding to object holder 212a on the thermal sensitive paper 208. The adjusted barcode 204 can be read by a device configured to read the barcode 204 and the medication information corresponding to the adjusted barcode 204 can be stored. In one embodiment, the adjustable barcode 204 can be utilized to indicate when the power source 206 expires.

Figure 4:
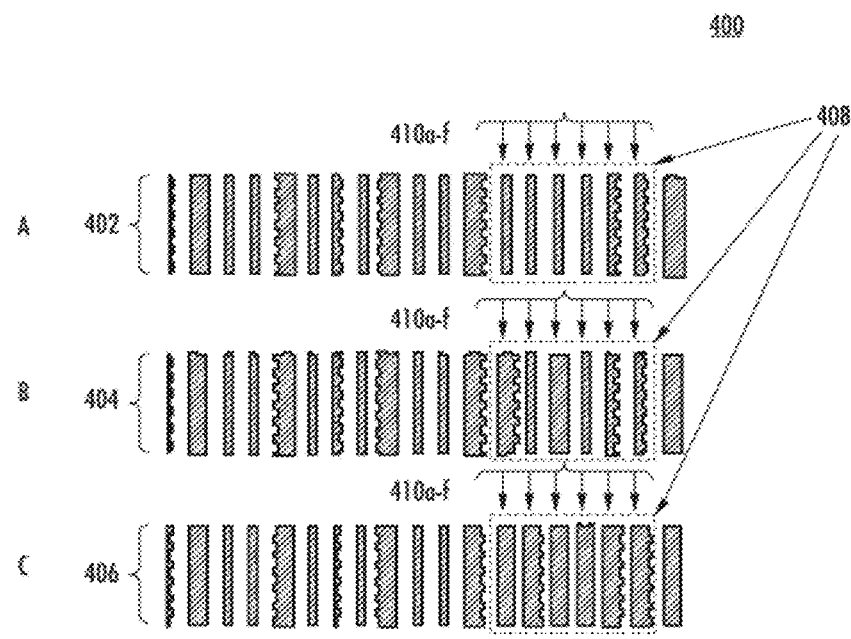
FIG. 4 is an illustration depicting various states of an adjustable barcode.

Referring now also to FIG. 4, an illustration depicting various states of an adjustable barcode 400 is shown. State (A) 402 illustrates the adjustable barcode 400 in a state where none of the "bits" 410a-f on the thermal paper 408 have been widened. This can indicate that the medication packaging featuring this state is either new or unused. State (B) 404 illustrates two "bits" 410a and 410c that have been widened on the thermal paper 408. Notably, the location of "bits" 410a and 410c can correspond to the location of resistive strips 210a and 210c from FIG. 2. Since the two "bits" 410a and 410c have been widened, this can indicate that medicine has been dispensed from object holders 212a and 212c, that the medications were taken out of sequence, and/or that one or more medications were not taken according to the required regimen. State (C) 406 illustrates the adjustable barcode 400 in a state where all object holders 212a-f have been dispensed, which can indicate an empty or tampered medication package.

Figure 5:
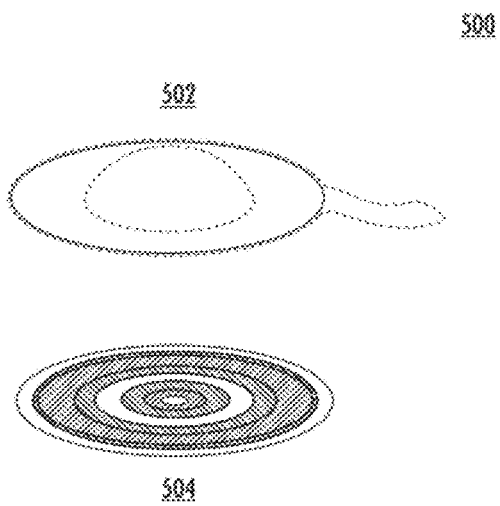
FIG. 5 is an illustration depicting a tear-away tab for use in medication monitoring.

According to another embodiment, the medication packaging 200 can include a tear-away structure for providing monitoring of medication compliance. The tear-away structure does not have to be electrical in nature. Referring now also to FIG. 5, an illustration depicting an object holder 500 including a tear-away tab 502 is shown. The tear-away tab 502 can be torn from a medication packaging to reveal an alternate color, shade, or pattern 504. This alternate color or pattern can serve as an indication to the patient that the medication corresponding to that particular spot on the medication packaging was dispensed. In another embodiment, when the tear-away tab 502 is torn off the medication packaging, it can reveal an alternate barcode, which can be read by a communications device or processor. The alternate barcode can provide dispensing information or other information.

Figure 6:
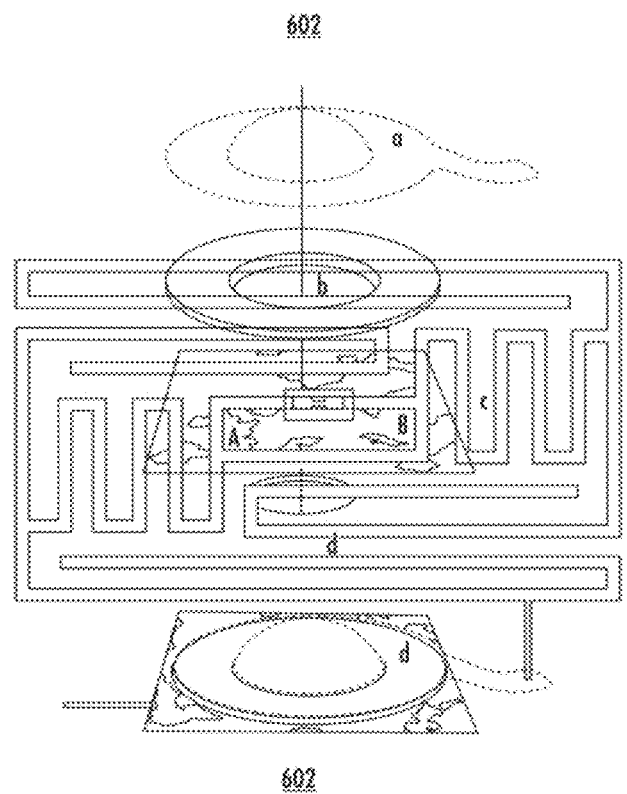
FIG. 6 is a schematic view illustrating the use of a radio frequency identification device (RFID) in a medication packaging, according to an embodiment of the invention

In another embodiment of the invention, the electrical contact created when the conducting cover 302 contacts the conductive foil 308 can be utilized to activate a RFID device, Bluetooth interface, and other remote connectivity means. Referring now also to FIG. 6, a schematic view illustrating the use of RFID in a medication packaging 600 is shown. RFID tags are typically passive resonant circuits, which can re-radiate with an active component powered by received energy. However, some tags are active and contain their own power source. The medication packaging 600 can include a tear-away tab structure/foil cover/shield 602, which when removed, as shown, can cause an RFID response. For example, by either covering an antenna pattern with the foil cover 602, changing resonance (by opening points A and B in FIG. 6), or by direct input to the active component to modulate and enable transmission, one can indicate that a medication has been dispensed or that the packaging has been tampered with, as packing removal exposes or modifies an RFID circuit. Also, RFID energy can be utilized for augmenting or replacing the power source 206 and/or to modify the barcode 204 for inventory purposes or preventing the sale of expired or tampered products.

Figure 7:
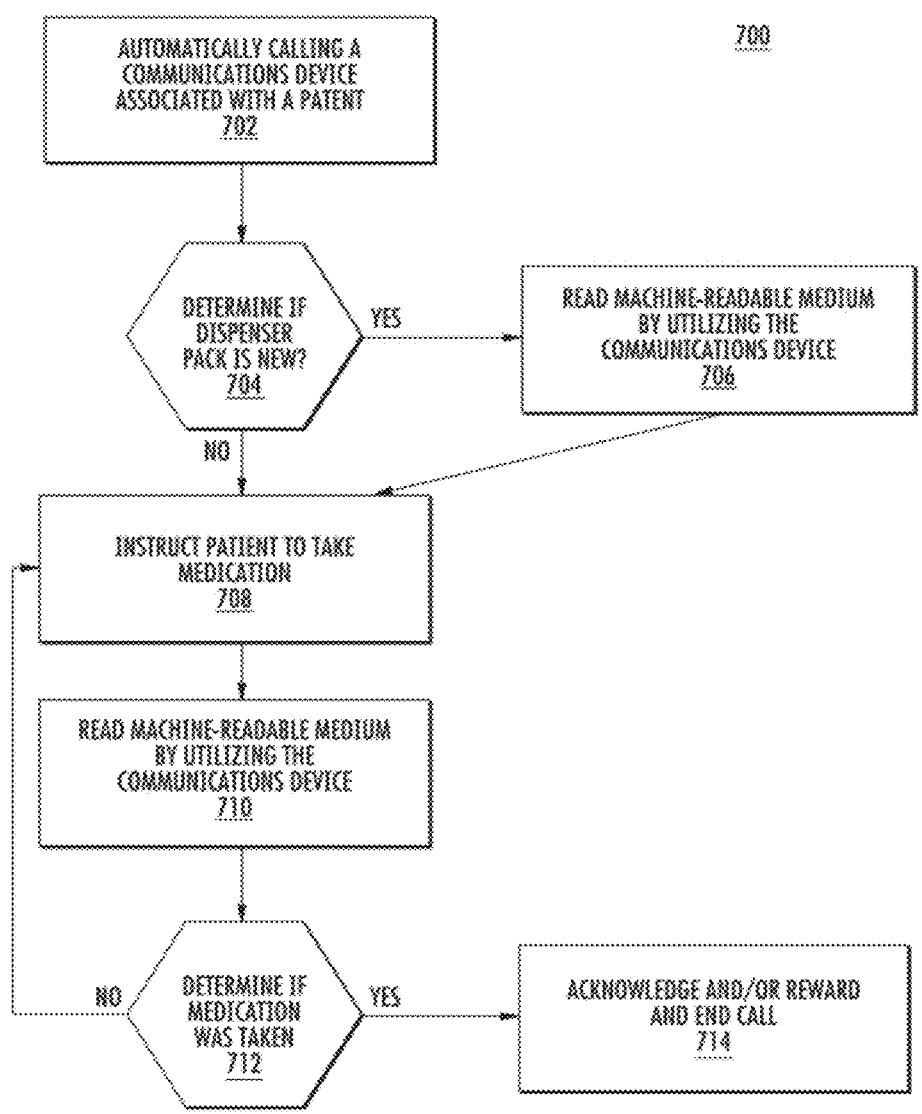
FIG. 7 is a flowchart of steps for monitoring and verifying medication compliance, according to a particular embodiment of the invention.

Referring now to FIG. 7, a flowchart of steps of method 700 for monitoring and verifying medication compliance in according with the system 100 is illustrated. The method 700 can include, at the start step 702, automatically calling the communications device 106 associated with patient by utilizing the processor 102. Also, the method can include determining if the medication packaging/dispenser pack is new at step 704. If the answer is yes, then the machine-readable medium can be read by communications device 106 at step 706. From here, the patient can be instructed to take medication at step 708. If the answer was no, the method 700 can proceed to instructing the user to take the medication without having to necessarily read the machine-readable medium.

Once the patient has been instructed to take the medication, the machine-readable medium can be read by utilizing the communications device 106 at step 710. It can then be determined whether the medication was dispensed or taken at step 712. If the medication was not dispensed or taken then the method can revert to step 708 and instruct the patient again. If the medication was dispensed, then the patient can receive an acknowledgement/verification, receive a reward, or have the call terminated at step 714.

Figure 8:
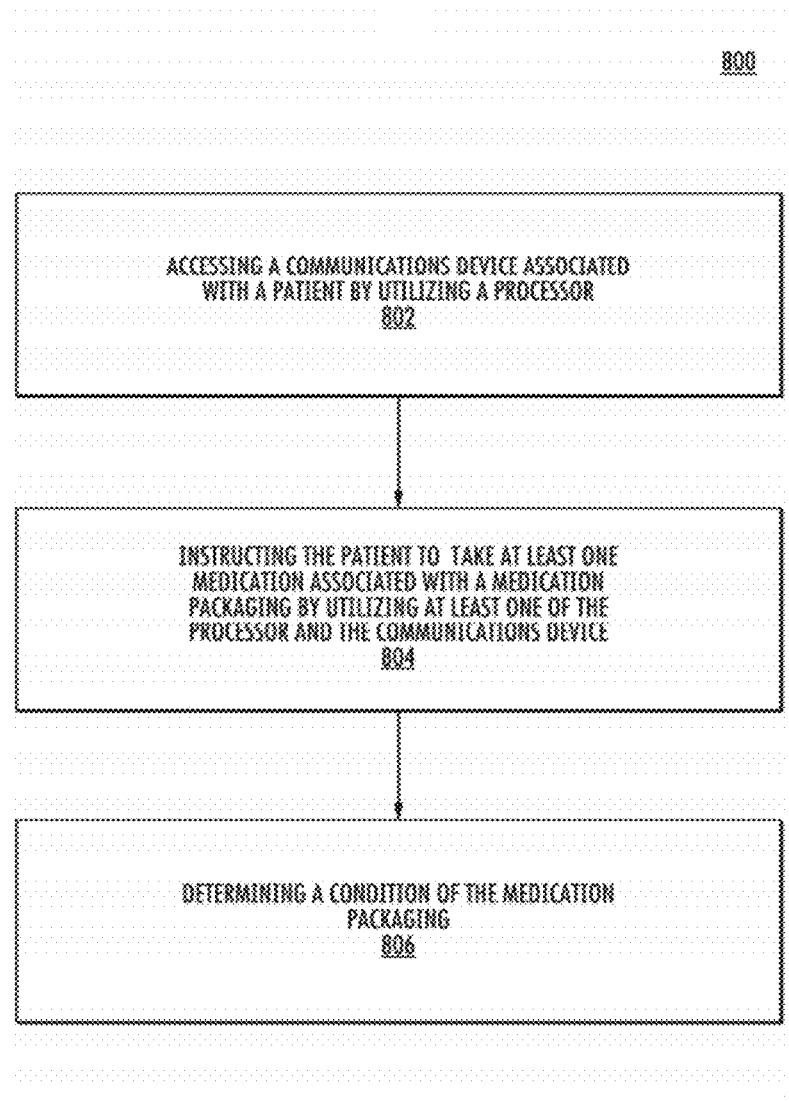
FIG. 8 is a flowchart of steps in a method for monitoring medication compliance, according to another embodiment of the invention.

Referring now to FIG. 8, a flowchart is provided that illustrates certain method aspects of the invention. The flowchart depicts steps of a method 800 for monitoring medication compliance. The method 800 illustratively can include, beginning at step 802, accessing a communications device associated with a patient by utilizing a processor. The method 800 can also include instructing the patient to take one or more medications associated with a medication packaging by utilizing one or more of the processor and the communications device at step 804. Furthermore, the method 800 can include determining a condition of the medication packaging at the concluding step 806.

According to a particular embodiment of the method 800, either the processor, the communications device, or both the processor and communications device can be configured to store, receive, and maintain medication information and/or information relating to the patient. In one embodiment, the condition of the medication packaging can indicate a dispensing of a medication of the one or more medications from the medication packaging, whether the one or more medications from the medication packaging has expired, and whether the medication packaging has been tampered with. In another embodiment, the method 800 can include acknowledging that a medication of the one or more medications was dispensed from the medication packaging. For example, the communications device can display an acknowledgment stating that the patient effectively dispensed the medication. The acknowledgement can also include notifying the patient through other means, such as through sound, printing out a confirmation, and the like.

The method 800 can also include rewarding the patient for having taken the medication or having dispensed the medication from the medication packaging. For example, the reward could be in the form of a coupon, which can be displayed on or printed from the processor or communications device and can be utilized to reduce the price of a future medication purchase. The method 800 can further include terminating access to the communications device after the determining step.

According to an embodiment, the medication packaging can comprise a machine-readable medium. The machine-readable medium can be a barcode, optical disk, magnetic disk, card, tape, magnetic strip, radio frequency tag, or other machine-readable medium. Notably, the machine-readable medium can comprise medication information and other information. For example, if the machine-readable medium is a barcode, the barcode can describe the medication in a manner that is consistent with the labeling on the package itself. In another embodiment, the machine-readable medium and corresponding medication information can be adjustable based on the dispensing of the medication from the medication packaging. For example, upon dispensing the medication from the packaging, the barcode can be altered or widened in such a way so as to indicate that the medication effectively dispensed.

In one embodiment, the method 800 can further include retrieving the medication information of the adjustable machine-readable medium by utilizing the communications device. For example, the communications device can have a built-in barcode reader to read the medication information from the adjusted or unadjusted machine-readable medium. Also, the communications device can also photograph and take an image of the adjusted or unadjusted machine-readable medium. Using the photograph, the communications device or the processor can read the information from the image.

In another embodiment, the method 800 can include determining if the medication packaging is in an unused state based on the retrieving step. The medication packaging can be in an unused state if the machine-readable medium has not been adjusted. As an illustration, if no medication has been dispensed, then the barcode would not be widened or altered. When the built-in reader reads the unadjusted barcode, it would indicate that the medication packaging had not been used by the patient. In yet another embodiment, the method 800 can include determining if a medication had been dispensed from the medication packaging, wherein the determination can be based on the retrieving step. In this case, the medication can be indicated as having been dispensed if a portion of the machine-readable medium corresponding to the one or more medications has been adjusted. In still another embodiment, the method 800 can include instructing the patient again to take the one or more medications if it is determined that the one or more medications has not been dispensed. It is important to note that the method 800 can incorporate aspects of other embodiments of the invention illustrated herein, such as those incorporated in the system 100.

In operation, a health care provider, such as a pharmacist with a barcode reader could scan a machine readable indicator on the medication package, such as a barcode on a blister pack. Alternatively, an image of the medication package can be captured by a camera in a mobile communications device. Additionally, a patient having access to a barcode reader could scan the barcode or position the medication package to a cell phone camera and the barcode can be deciphered by the system or a medical web service. In another operation of the present invention, a pen type bar code reader coupled with a cell phone device can be used to process the barcode of medication dosage compliance. Prescription errors and lack of patient compliance are important factors in medical errors and improper recovery. Benefits of the present invention include a legal digital record of compliance that indicates to both patients and health care providers that the correct medicine was taken at the correct time.

In another embodiment, a method for medication compliance can include supplying to a patient a medication package including a machine readable indicator of medication dosage compliance. The machine readable indicator can generate medication compliance information associated with the patient. For example, the machine readable indicator can be a barcode, optical disk, magnetic disk, card, tape, magnetic strip, radio frequency tag, or other machine-readable medium. The machine readable indicator can include medication compliance information. The method can also include providing a communications device capable of accessing and obtaining the medication compliance information from the medication package. Finally, the method can include sending the obtained medication compliance information to a processor for managing medication compliance information associated with the patient. Alternatively, the processor can be configured to interpret the machine readable indicator, such as a barcode. Responsive to determining that a patient has complied with properly taking medication, either the health care provider or the processor can send the patient a positive message confirming proper compliance by the patient.

In yet another embodiment, a medication compliance monitoring system or device can be provided. The system can include a medication package having at least one compartment which is yieldable for medication removal, such as a blister pack. The system can also include a machine readable indicator including medication compliance information, disposed on the medication package such that removal of a unit dose of medication from each compartment will cause a transformation of the machine readable indicator. The transformation can include the medication compliance information associated with the patient being updated based on the transformation of the machine readable indicator. The system can also include a communications device configured for obtaining the medication compliance information from the medication package. Furthermore, a processor can be configured for receiving the obtained medication compliance information from the communications device for managing medication compliance information associated with the patient. The processor can be communicatively linked to a storage medium, such as memory and can include program code enabled to supply to a patient a medication package including a machine readable indicator of medication dosage compliance, the indicator generating medication compliance information associated with the patient. Program code enabled to provide a communications device capable of accessing and obtaining the medication compliance information from the medication package can be provided. Additionally, sending the obtained medication compliance information to the processor for managing medication compliance information associated with the patient can be included in the program code.

The invention can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, (defining a computer program) which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding description of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A computer-based method for monitoring medication compliance, the method comprising the steps of:
   accessing a communications device associated with a patient by utilizing a processor;
   via at least one of the processor and the communications device, instructing the patient to take at least one medication associated with a medication packaging having a machine-readable medium storing medication information that is adjustable based on a dispensing of the at least one medication from the medication packaging and to capture and store an image of the medication information; and
   determining a condition of the medication packaging based on the medication information, wherein the medication information is retrieved from the image by utilizing the communications device.

2. The method of claim 1, wherein at least one of the processor and the communications device are configured to store, receive, and maintain at least one of medication information and information relating to the patient.

3. The method of claim 1, wherein the condition of the medication packaging indicates at least one of a dispensing of a medication of the at least one medication from the medication packaging, whether the at least one medication of the medication packaging has expired, and whether the medication packaging has been tampered with.

4. The method of claim 3, further comprising performing at least one of acknowledging that the medication of the at least one medication was dispensed from the medication packaging, rewarding the patient, and terminating access to the communications device after the determining step.

5. The method of claim 1, further comprising determining if the medication packaging is in an unused state based on the retrieving step, wherein the medication packaging is in an unused state if the machine-readable medium has not been adjusted.

6. The method of claim 1, further comprising determining if the medication of the at least one medication has been dispensed from the medication packaging based on the retrieving step, wherein the medication of the at least one medication has been dispensed if a portion of the machine-readable medium corresponding to the at least one medication has been adjusted.

7. The method of claim 6, further comprising instructing the patient again to take the at least one medication if it is determined that the at least one medication has not been dispensed.

8. A computer-based system for monitoring medication compliance, the system comprising:
   at least one processor configured to process and manage data;
   at least one communications device communicatively linked to the at least one processor; and
   at least one medication packaging comprising a machine-readable medium,
   wherein the machine-readable medium comprises medication information;
   wherein the at least one processor is configured to: receive the medication information of the machine-readable medium, wherein the machine-readable medium and corresponding medication information are adjustable based on a dispensing of a medication from the at least one medication packaging;
   wherein the at least one communications device captures and stores an image of the adjustable machine-readable medium; and wherein the at least one communications device retrieves the medication information from the image.

9. The system of claim 8, wherein the at least one communications device is configured to forward the medication information to the at least one processor.

10. The system of claim 8, wherein the at least one communications device comprises a reader configured to retrieve the medication information from the adjustable machine-readable medium.

11. The system of claim 8, wherein at least one of the at least one processor and the at least one communications device is configured to determine if the at least one medication packaging is in an unused state, wherein the at least one medication packaging is in an unused state if the machine-readable medium has not been adjusted.

12. The system of claim 8, wherein at least one of the at least one processor and the at least one communications device is configured to determine if the medication has been dispensed from the at least one medication packaging, wherein the medication has been dispensed if a portion of the machine-readable medium corresponding to the medication has been adjusted.

13. The system of claim 8, wherein at least one of the at least one processor and the at least one communications device is configured to perform at least one of acknowledging that the medication was dispensed from the at least one medication packaging and providing a reward.

14. The system of claim 8, wherein the machine-readable medium is at least one of a barcode, optical disk, magnetic disk, card, tape, magnetic strip, radio frequency tag, and other machine-readable medium.

15. A medication packaging, the medication packaging comprising:
   at least one object holder;
   a thermal sensitive paper; and
   a machine-readable medium operably coupled to the at least one object holder,
   wherein the machine-readable medium is adjustable upon dispensing an object from the at least one object holder; wherein the machine-readable medium comprises a barcode; and wherein the thermal sensitive paper resides over an array of resistive strips residing adjacent to a portion of the barcode.

16. The medication packaging of claim 15, wherein the object is a medication.

17. The medication packaging of claim 16, wherein the medication is at least one of a pill and a liquid.

18. The medication packaging of claim 15, wherein the machine-readable medium further comprises at least one of an optical disk, magnetic disk, card, tape, magnetic strip, or radio frequency tag.

19. The medication packaging of claim 15, further comprising a power source operably coupled to the array of resistive strips and to the at least one object holder, wherein the at least one object holder comprises a conductive cover, an insulator, and a conductive foil.

20. The medication packaging of claim 19, wherein the conductive cover, upon being depressed, causes the conductive foil to tear and release the object from the at least one object holder.

21. The medication packaging of claim 20, wherein the conductive cover contacts the conductive foil thereby closing a circuit with the power source.

22. The medication packaging of claim 21, wherein the closed circuit causes at least one resistive strip of the array of resistive strips to heat and self-destruct, thereby causing the at least one resistive strip to alter the thermal sensitive paper to create a readable image on the thermal sensitive paper.

23. The medication packaging of claim 22, wherein the readable image can adjust the barcode and indicate which object has been dispensed, and wherein the barcode can be read by a device configured to retrieve information from the barcode.

24. The medication packaging of claim 21, wherein the contact is utilized to activate at least one of a radio frequency device, Bluetooth interface, and other remote connectivity means.

25. A storage medium having stored therein machine-readable instructions to, which, when loaded in and executed by a computer, causes the computer to perform the steps of:
   accessing a communications device associated with a patient by utilizing a processor;
   via at least one of the processor and the communications device, instructing the patient to take at least one medication associated with a medication packaging having a machine-readable medium storing medication information that is adjustable based on a dispensing of the at least one medication from the medication packaging and to capture and store an image of the medication information; and
   determining if the medication was dispensed from the medication packaging based on the medication information, wherein the medication information is retrieved from the image by utilizing the communications device.

26. A computer-based method for medication compliance, the method comprising the steps of:
   supplying to a patient a medication package including a machine readable indicator of medication dosage compliance, said indicator adjustable based on a dispensing of at least one medication from the medication packaging, and the adjusting of said indicator generating medication compliance information associated with the patient;
   providing a communications device capable of accessing said medication compliance information;
   obtaining said medication compliance information from the medication package with the communications device, wherein said obtaining comprises storing image data for said indicator retrieving the medication compliance information from the image data; and
   sending the obtained medication compliance information to a processor for managing medication compliance information associated with the patient.

27. A medication compliance monitoring device, comprising:
   a medication package comprising at least one compartment which is yieldable for medication removal;
   a machine readable indicator including medication compliance information disposed on said medication package such that removal of a unit dose of medication from said compartment will cause a transformation of said machine readable indicator, wherein the medication compliance information associated with the patient becomes updated based on the transformation of said machine readable indicator;
   a communications device configured for obtaining said medication compliance information from said medication package, wherein said obtaining comprises storing image data for said machine readable indicator retrieving the medication compliance information from the image data;
   a processor configured for receiving the obtained medication compliance information from the communications device for managing medication compliance information associated with the patient.

* * * * *